United States Patent
Ryu et al.

(10) Patent No.: US 10,695,394 B2
(45) Date of Patent: Jun. 30, 2020

(54) COMPOSITION CONTAINING HERBAL MEDICINE EXTRACTS OF PINELLIA AND SCUTELLARIA FOR REDUCING SIDE EFFECTS DUE TO ANTICANCER DRUGS

(71) Applicant: COMPREHENSIVE AND INTEGRATIVE MEDICINE INSTITUTE, Daegu (KR)

(72) Inventors: Heon Mo Ryu, Daegu (KR); Dae Jun Kim, Daegu (KR); Joon Seok Byun, Daegu (KR); Ki Cheul Sohn, Daegu (KR); Sae Kwang Ku, Daegu (KR)

(73) Assignee: COMPREHENSIVE AND INTEGRATIVE MEDICINE INSTITUTE, Daegu (KR)

( * ) Notice: Subject to any disclaimer, the term of this patent is extended or adjusted under 35 U.S.C. 154(b) by 170 days.

(21) Appl. No.: 15/963,424

(22) Filed: Apr. 26, 2018

(65) Prior Publication Data

US 2018/0289763 A1   Oct. 11, 2018

Related U.S. Application Data

(63) Continuation of application No. 14/893,876, filed as application No. PCT/KR2014/004548 on May 21, 2014, now abandoned.

(30) Foreign Application Priority Data

May 30, 2013  (KR) ........................ 10-2013-0062034

(51) Int. Cl.
  *A61K 36/00*   (2006.01)
  *A61K 36/8888*  (2006.01)
  *A61K 36/539*  (2006.01)

(52) U.S. Cl.
  CPC ........ *A61K 36/8888* (2013.01); *A61K 36/539* (2013.01)

(58) Field of Classification Search
  CPC ..................................................... A61K 36/00
  See application file for complete search history.

(56) References Cited

FOREIGN PATENT DOCUMENTS

| CN | 1762424 A | 4/2006 |
|---|---|---|
| CN | 100998805 A * | 7/2007 |
| CN | 101461844 A | 6/2009 |
| CN | 102100844 A | 6/2011 |
| KR | 10-2002-0086627 A | 11/2002 |
| KR | 101133837 B1 | 4/2012 |

OTHER PUBLICATIONS

International Search Report for International Application No. PCT/KR2014/004548 (2 Pages) (dated Sep. 12, 2014).
Li et al., "Medicine property variation in different proportional combinations of Scutellariae Radix and prepared Pinellia tuber through determination leaching quantity of baicalin by HPLC", Chinese Journal of Experimental Traditional Medical Formulae, 2011, vol. 17, No. 17, pp. 116-118.
Minematsu et al., "A Subchronic 3-Month Oral Toxicity Study of Tsumura Sho-Saiko-To T J-9 in the Rat Via Oral Gavage Administration With a 4-Week Recovery Period", Oyo Yakuri, 1992, vol. 43, No. 1, pp. 19-42.

* cited by examiner

*Primary Examiner* — Qiuwen Mi
(74) *Attorney, Agent, or Firm* — Lucas & Mercanti, LLP (57) ABSTRACT

The present invention relates to a composition containing a Pinelliae Rhizoma and Scutellariae Radix extract as an active ingredient to reduce side effects caused by an anticancer drug, and more particularly, a composition for reducing side effects such as damage to the gastrointestinal tract and a gastrointestinal motility disorder by administering an anticancer drug. The composition of the present invention has an excellent effect of reducing side effects in administration of the anticancer drug through an antioxidative function, and synthesis, secretion and control of the functions of gastrin and serotonin producing gastrointestinal endocrine cells.

3 Claims, 7 Drawing Sheets

COMPOSITION CONTAINING HERBAL MEDICINE EXTRACTS OF PINELLIA AND SCUTELLARIA FOR REDUCING SIDE EFFECTS DUE TO ANTICANCER DRUGS

CROSS-REFERENCE TO RELATED APPLICATIONS

This application is a continuation of U.S. application Ser. No. 14/893,876, filed Nov. 24, 2015, which in turn is a 371 of PCT/KR2014/004548, filed May 21, 2014, which claims the benefit of Korean Patent Application No. 10-2013-0062034, filed May 30, 2013, the contents of each of which are incorporated herein by reference.

TECHNICAL FIELD

The present invention relates to a composition containing a Pinelliae Rhizoma and Scutellariae Radix extract as an active ingredient to reduce side effects caused by an anticancer agent.

BACKGROUND ART

Cisplatin is a representative platinum-complex anticancer drug containing platinum II in its center and a widely-used chemotherapeutic agent to treat a variety of tumors, and has shown a relatively excellent anticancer effect. However, as serotonin is synthesized and serotonin $5\text{-}HT_3$ receptors are activated in endocrine cells present in the digestive tract, gastrointestinal motility as well as damage to the gastrointestinal tract are considerably inhibited, thereby causing a variety of toxicities in the gastrointestinal tract, for example, gastric stasis of food. Particularly, cisplatin serves as a representative redox cycler producing active oxygen species (Chirino and Pedraza-Chaverri, 2009) to cause damage to the function and DNA of gastrointestinal mucosal cells, and therefore it is known to cause a digestive disorder, particularly, a motility disorder (Chang et al., 2002).

Accordingly, in tumor treatment by cisplatin, the control of side effects of a digestive system is a very important aspect to utilize a potent anticancer effect of the drug, and in development of various drugs for the digestive system including a current antiemetic, cisplatin is used to induce a representative model of a digestive system disorder, and various $5\text{-}HT_3$ receptor blocking agents, antiphlogistic drugs and antioxidants have useful effects on a gastrointestinal disorder caused by the cisplatin treatment.

Meanwhile, gastrin is a representative hormone, which is produced and secreted from digestive tract endocrine cells focally present in gastric mucosa, particularly, pyloric mucosa, and stimulates gastric acid secretion so as to increase a gastric digestive function. A gastrointestinal motility disorder, particularly, a decrease in gastrointestinal motility is caused by cisplatin, and as a result, gastrin production is considerably reduced, thereby further increasing indigestion or compaction.

Also, it is known that, today, 90% or more serotonin is present in the digestive tract, and the serotonin present in the gastrointestinal tract is synthesized by tryptophan hydroxylase, mostly stored in gastrointestinal tract endocrine cells present in mucous epithelium, that is, enterochromaffin cells, and then secreted from gastrointestinal tract endocrine cells to a matrix due to various stimuli. It is known that the secreted serotonin generally enters gastrointestinal tract mucous epithelial cells by a serotonin re-uptake transporter, and then removed by being degraded into 5-hydroxyindoleacetic acid by an intracellular enzyme, monoamine oxidase, present in digestive tract mucosa and a tissue underneath the mucosa. Meanwhile, it is known that cisplatin serves to synthesize serotonin of endocrine cells present in the digestive tract and activate serotonin $5\text{-}HT_3$ receptors, or inhibit activity of the intracellular enzyme serving to degrade serotonin, monoamine oxidase, thereby considerably inhibiting the gastrointestinal motility as well as the damage to the gastrointestinal tract.

Meanwhile, Pinelliae Rhizoma is a sour herbal medicine, and is known to be warm in nature, dry, and effective in the spleen, stomach and lung. The Pinelliae Rhizoma has warm and dry properties, and thereby has an effect of eliminating dampness and abating phlegm. Therefore, the Pinelliae Rhizoma is an important herb for eliminating phlegm, and abating the counterflow of energy (qi). The Pinelliae Rhizoma also has effects of inhibiting coughing, lowering the energy (qi) of the lung, increasing an appetite, activating the spleen, and removing excessive phlegm and a bloated feeling from the chest.

In addition, the herbal medicine, Scutellariae Radix, is the root of *Scutellaria baicalensis*, and has a bitter taste and a cold property. The herbal medicine, Scutellariae Radix, is generally used in lung, gall bladder, and large intestine treatment, and specifically, has effects of eliminating dampness and heat, compensating for toxicity, and arresting hemorrhaging.

DISCLOSURE

Technical Problem

To solve the conventional technical demands, the present invention is directed to providing a composition for reducing side effects caused by an anticancer drug, which uses a Pinelliae Rhizoma and Scutellariae Radix extract.

However, technical objects to be accomplished in the present invention are not limited to the above-described object, and other objects which will not be described will be clearly understood to those of ordinary skill in the art from the following descriptions.

Technical Solution

To accomplish the object, the present invention provides a composition containing a Pinelliae Rhizoma and Scutellariae Radix extract to reduce side effects caused by an anticancer drug.

In one exemplary embodiment of the present invention, the anticancer drug is cisplatin.

In another exemplary embodiment of the present invention, a mixing weight ratio of the Pinelliae Rhizoma and Scutellariae Radix extract is 0.1 to 5:0.5 to 6.

Advantageous Effects

A composition for reducing side effects caused by an anticancer drug, which contains a Pinelliae Rhizoma and Scutellariae Radix extract as an active ingredient, according to the present invention has an effect of reducing side effects such as damage to the gastrointestinal tract and a gastrointestinal motility disorder, which are caused by administration of the anticancer drug. The composition of the present invention has an excellent effect of reducing the side effects caused in the administration of the anticancer drug through an antioxidative function, and synthesis, secretion, and control of a function of gastrin and serotonin-producing gastrointestinal endocrine cells.

MODES OF THE INVENTION

As a result of efforts to develop a composition capable of reducing various side effects caused by administration of an anticancer drug in order to treat a neoplastic disease, the inventors focused on Oriental medicine, and found that a Pinelliae Rhizoma and Scutellariae Radix extract among the Oriental medicine has an excellent effect of reducing side effects caused by an anticancer drug.

Therefore, the present invention is directed to providing a composition containing a Pinelliae Rhizoma and Scutellariae Radix extract as an active ingredient to reduce side effects caused by an anticancer drug.

The term "Pinelliae Rhizoma and Scutellariae Radix extract" used herein refers to a mixture of drug extracts extracted from Pinelliae Rhizoma and Scutellariae Radix. The extract is obtained by washing dry medical herbs, Pinelliae Rhizoma and Scutellariae Radix, with water, mixing the Pinelliae Rhizoma with the Scutellariae Radix in a weight ratio (w/w) of 0.1 to 5:0.5 to 6, preferably, 1 to 3:2 to 4, and extracting the mixture with a 5 to 20-fold weight (w/v) of water, methanol, ethanol or a mixed solvent. Preferably, the mixture is extracted with water, but the present invention is not limited thereto. The extraction may be performed by hot water extraction, macerating extraction, or ultrasound-associated extraction at 40 to 150° C., preferably 70 to 130° C. for 30 minutes to 6 hours, preferably 1 to 4 hours. The hot water extraction is preferably used, but the present invention is not limited thereto. A liquid extract may be filtered using filter paper, and the obtained filtrate undergoes lyophilization, room temperature drying, or hot-air drying, preferably lyophilization, thereby obtaining a herb extract consisting of the Pinelliae Rhizoma and Scutellariae Radix of the present invention.

In an exemplary embodiment of the present invention, the anticancer drug may be cisplatin, but if the anticancer drug is, particularly, a chemotherapeutic agent, the present invention is not limited thereto.

Particularly, the composition of the present invention has a great effect on a gastrointestinal disorder caused by the anticancer drug.

The Pinelliae Rhizoma and Scutellariae Radix extract is administered after administration of the anticancer drug, and thus has an effect of reducing side effects. The duration of extract administration may be performed within 5 minutes to 4 hours, preferably, 10 to 50 minutes, and most preferably, 30 minutes, after the administration of the anticancer drug, but the present invention is not limited thereto.

The anticancer drug and the Pinelliae Rhizoma and Scutellariae Radix extract may be parenterally, orally, locoregionally or percutaneously administered. The Pinelliae Rhizoma and Scutellariae Radix extract may be orally administered, but the administration route may be suitably selected by those skilled in the art depending on a patient's condition and body weight, severity of a disease, and a duration of administration.

The composition of the present invention may include a pharmaceutically acceptable carrier. The pharmaceutically acceptable carrier may include a saline solution, polyethyleneglycol, ethanol, a vegetable oil, isopropylmyristate, and the like, but the present invention is not limited.

In an exemplary embodiment of the present invention, a preferable dose of the composition may be vary depending on a patient's condition and body weight, severity of a disease, a dosage form, and administration route and duration, but may be suitably selected by those skilled in the related art. However, the composition may be administered daily at a dose of 0.001 to 300 mg/kg (body weight), preferably, 0.01 to 200 mg/kg (body weight), and most preferably, 50 to 200 mg/kg (body weight) as shown in an example of the present invention. However, the present invention is not limited thereto.

The pharmaceutical composition according to the present invention may be administered to a mammal such as a rat, a mouse, livestock, and a human through various routes of administration. Methods of administration are not particularly limited. For example, the composition may be administered orally, or rectally, or by intravenous, intramuscular, subcutaneous, cervical epidural, or intracerebroventricular injection.

In other words, the composition containing the Pinelliae Rhizoma and Scutellariae Radix extract of the present invention to reduce side effects caused by an anticancer drug may reduce side effects, such as a gastroenteric disorder, caused when the anticancer drug is administered alone.

Hereinafter, exemplary embodiments according to the present invention will be provided to help understanding of the present invention. However, the following examples are merely provided such that the present invention can be more easily understood, and the scope of the present invention is not limited to the following examples.

EXAMPLES

In the examples, to provide an integrated medical method to reduce side effects caused by a chemotherapeutic agent with respect to a patient with a neoplastic disease, an effect of co-administration of a Pinelliae Rhizoma and Scutellariae Radix extract with respect to a digestive motility disorder caused by the chemotherapeutic agent was examined. In the following examples, rats with a gastrointestinal motility disorder caused by cisplatin were used. 2 mg/kg of cisplatin was administered once a week for 5 weeks, each of 200, 100 and 50 mg/kg of the Pinelliae Rhizoma and Scutellariae Radix extracts were administered at 14 days from the fourth administration of cisplatin, influences on gastrointestinal motility, damage to a digestive tract mucosa and physiology of digestive tract endocrine cells were observed as well as an antioxidative effect, experimental results were compared to an ondansetron 1 mg/kg administered group, wherein the ondansetron was known as a representative 5-$HT_3$ receptor blocking agent to have an effective effect on a cisplatin-induced gastrointestinal motility disorder.

Figure 1:
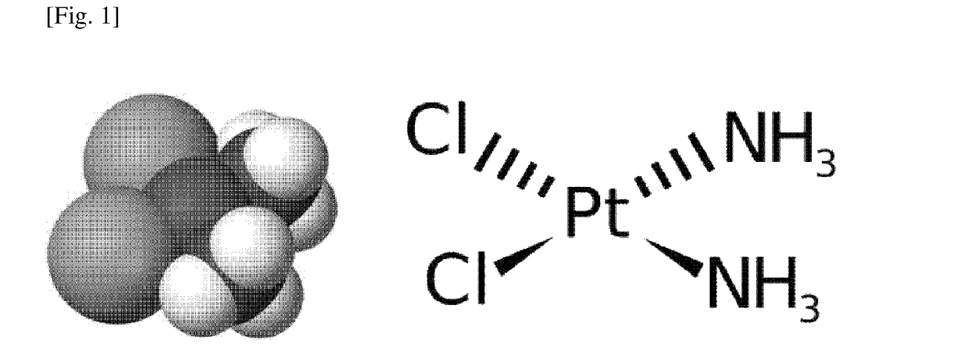
FIG. 1 shows the structure of cisplatin, which is an anticancer drug used in the present invention.

The chemotherapeutic agent for treating cancer used in the examples was cis-diaminedichloroplatinum II (cisplatin; Sigma-Aldrich, St. Louis, Mo., USA), and the structure thereof is shown in FIG. 1. Also, the Pinelliae Rhizoma and Scutellariae Radix extract (hereinafter, referred to as PS) was purchased from Hanzung Pharmaceutical Co. Ltd, and the composition thereof is shown in Table 1.

TABLE 1

| Herbs | Scientific Names/Produce Region | Amounts (g) |
| --- | --- | --- |
| Pinelliae Rhizoma | *Pinellia ternata* (Thunb.) Breitenb. | 1.34 |
| Scutellariae Radix | *Scutellaria baicalensis* Georgi | 1.80 |
| Total | 2 types | 3.14 |

Example 1. Preparation and Method of Experiment 1.1. Preparation of Laboratory Animals In this example, as laboratory animals, Sprague-Dawley, Slc: SD rats (6-week-old males, SLC, Shizuoka, Japan) were used. 60 healthy SPF rats were purchased, acclimated for 14 days, and 8 laboratory animals having uniform body weights (intact control: 249.13±12.12 g, 232~264 g; cisplatin treated group: 225.35±10.58 g, 206~243 g) when fasting after three weeks of cisplatin administration per each group were selected to be used in the experiment. As shown in Table 2, the laboratory animals were divided into 6 groups. All of the laboratory animals underwent fasting for about 18 hours at each of the first treatment of cisplatin, the first drug administration and the final necropsy (even in this period, drinking water was freely provided), individuals were identified using picric acid.

To cause a gastrointestinal motility disorder, 2 mg/kg of cisplatin (Sigma-Aldrich, St. Louise, Mo., USA) was dissolved in a saline solution, and the resulting solution was intraperitoneally administered at a dose of 1 ml/kg once a week for 5 weeks, thereby causing a chronic gastrointestinal motility disorder, and in the normal vehicle control, the same dose of a saline solution, instead of cisplatin, was intraperitoneally administered by the same method.

A Pinelliae Rhizoma and Scutellariae Radix herbal medicine was dissolved in sterile distilled water at a dose of 5 ml/kg (a body weight of the animal) three weeks after the first cisplatin administration, and forcibly and orally administered with a 5 ml syringe equipped with a metal zonde 30 minutes after the fourth cisplatin administration once a day for 14 days. The ondansetron was dissolved in a saline solution, subcutaneously administered with the same frequency as the Pinelliae Rhizoma and Scutellariae Radix herbal medicine at a dose of 1 ml/kg, and in the normal vehicle and cisplatin controls, instead of the Pinelliae Rhizoma and Scutellariae Radix extract or ondansetron, only the same dose of sterile distilled water was orally administered. A dose of the ondansetron used in the experiment was selected to be 1 mg/kg (Malik et al., 2007) which is known to show a positive effect on the digestive disorder conventionally caused by cisplatin, and doses of the Pinelliae Rhizoma and Scutellariae Radix extract were also selected to be 200, 100 and 50 mg/kg based on a previous experiment of examining an effect of stimulating rat gastrointestinal motility (Lee et al., 2006).

TABLE 2

| Group | Inducer | Test substances and dose (mg/kg/day) | Animal No. |
| --- | --- | --- | --- |
| Effects on cisplatin-induced GI disorders in rats ||||
| Control | Saline 1 ml/kg | Distilled water 10 ml/kg | R01~R08 |
| Control | Cisplatin 2 mg/kg | Distilled water 10 ml/kg | R09~R16 |
| Reference | Cisplatin 2 mg/kg | Ondansetron subcutaneous (1 mg/kg) | R17~R24 |
| Active | Cisplatin 2 mg/kg | PS oral (200 mg/kg) | R25~R32 |
| Active | Cisplatin 2 mg/kg | PS oral (100 mg/kg) | R33~R40 |
| Active | Cisplatin 2 mg/kg | PS oral (50 mg/kg) | R41~R48 |

1.2. Observation Items

An effect on the gastrointestinal motility was evaluated by evaluating a charcoal transit ratio in the small intestine, effects on constipation were evaluated by observing a body weight, the change in fecal parameters (the fecal pellet number, the fecal weight, and the water content in the feces), the histopathological changes in the colon containing fecal pellets—changes in fecal pellet surface mucosa thickness, mucous producing cell number per mm2 of the mucosa and average mucosa thickness. Also, to evaluate the influence on damage to the mucosa of the digestive tract and physiology of digestive tract endocrine cells, changes in thicknesses and damaged area ratio of fundic, pyloric and colonic mucosa, changes in gastrin and serotonin immunoreactive cells in the pyloric mucosa, changes in serotonin immunoreactive cells in the colonic mucosa, changes in pylorus gastrin and serotonin contents, and changes in activities of serotonin metabolism-associated enzymes—tryptophan hydroxylase and monoamine oxidase were observed. To observe an antioxidative effect, the contents of glutathione (GSH), superoxide dismutase (SOD) and catalase (CAT) of the fundus were measured, and to observe the influence on lipid peroxidation, malondialdehyde (MDA) content was measured.

Example 2. Confirmation of Changes in Body Weight and Body Weight Gain

Body weights and body weight gains in each group that were measured after the first and fourth administrations of cisplatin and the necropsy are shown in Table 3.

TABLE 3

| Groups | Body weight (g) | | | Body weight gain (g) | |
|---|---|---|---|---|---|
| | At first cisplatin treatment [A] | At 4th cisplatin treatment [B] | Sacrifice [C] | Total experiment periods [C − A] | Test article dosing periods [C − B] |
| Controls | | | | | |
| Intact | 198.38 ± 12.82 | 249.13 ± 12.12 | 252.88 ± 13.51 | 54.50 ± 5.13 | 3.75 ± 2.87 |
| Cisplatin | 199.13 ± 14.12 | 225.00 ± 13.90$^a$ | 195.13 ± 12.96$^a$ Reference | −4.00 ± 7.01$^d$ | −29.88 ± 3.04$^d$ |
| Ondansetron | 197.88 ± 11.37 | 226.88 ± 6.60$^a$ | 212.38 ± 4.66$^{ab}$ | 14.50 ± 11.64$^{de}$ | −14.50 ± 5.68$^{de}$ |
| PS orally administered | | | | | |
| 200 mg/kg | 199.13 ± 12.02 | 223.63 ± 12.28$^a$ | 231.75 ± 12.89$^{ab}$ | 32.63 ± 10.27$^{de}$ | 8.13 ± 8.22$^e$ |
| 100 mg/kg | 199.38 ± 10.46 | 226.38 ± 11.29$^a$ | 218.50 ± 6.89$^{ab}$ | 19.13 ± 6.62$^{de}$ | −7.88 ± 6.40$^{de}$ |
| 50 mg/kg | 198.25 ± 15.07 | 224.88 ± 10.08$^a$ | 212.00 ± 8.78$^{ac}$ | 13.75 ± 13.12$^{df}$ | −12.88 ± 9.58$^{de}$ |

Figure 2:
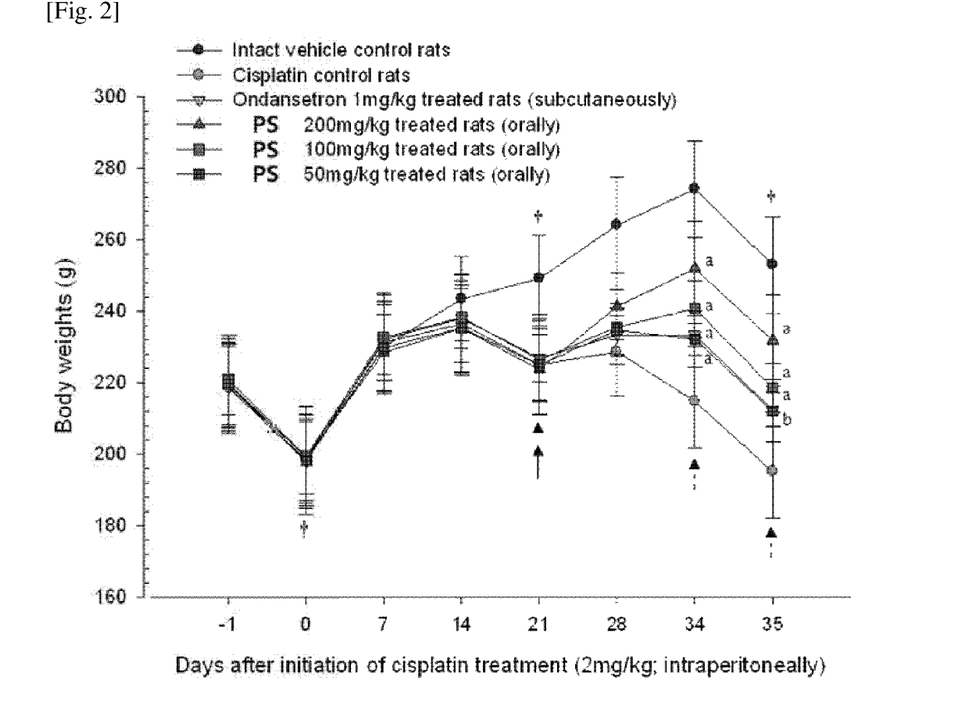
FIG. 2 shows the change in body weights of laboratory animals of each group for 5 weeks.

Three weeks after the first cisplatin administration, laboratory animals having similar body weights were selected and used. Compared to the normal vehicle control, in the cisplatin control, a significantly (p<0.01) considerable decrease in body weight was shown three weeks after the cisplatin administration, that is, from the first day of administration, and therefore, the body weight gains during the total five-week experiment and for two weeks of the drug administration also showed significantly (p<0.01) considerable decreases in the cisplatin control, compared to the normal vehicle control. Meanwhile, in the ondansetron and three doses (200 mg/kg, 100 mg/kg and 50 mg/kg) of the Pinelliae Rhizoma and Scutellariae Radix extract-treated groups, compared to the cisplatin control, significant (p<0.01 or p<0.05) increases in body weight were shown 13 and 14 days after the drug administration, and significant (p<0.01) increases in body weight gains during the total period of the experiment and the drug administration were also shown in the ondansetron and three doses of the Pinelliae Rhizoma and Scutellariae Radix extract-treated groups, compared to the cisplatin control (FIG. 2).

In the cisplatin control, compared to the normal vehicle control, the body weight gain for 2 weeks after the drug administration changed by −896.67%, and in the ondansetron, and Pinelliae Rhizoma and Scutellariae Radix extract 200, 100 and 50 mg/kg administered groups, compared to the cisplatin control, the body weight gains changed by 52.46, 128.20, 74.64 and 57.90%, respectively.

In the cisplatin control, compared to the normal vehicle control, the body weight gain during the total 5-week experiment changed by −107.34%, and in the ondansetron, and Pinelliae Rhizoma and Scutellariae Radix extract 200, 100 and 50 mg/kg administered groups, compared to the cisplatin control, the body weight gains changed by 463.50, 916.63, 579.13 and 444.75%, respectively.

The cisplatin serving as a representative redox cycler (Chirino and Pedraza-Chaverri, 2009), caused direct damage to various organs of the body, and therefore a considerable decrease in body weight was achieved (Suddek et al., 2011; Khan et al., 2012; Naqshbandi et al., 2012). Even in this experiment, after the cisplatin administration, a considerable decrease in body weight was achieved, and three weeks after the first administration of cisplatin, laboratory animals having similar body weights were selected and used. Meanwhile, in the ondansetron and all of three doses of the Pinelliae Rhizoma and Scutellariae Radix extract treated groups, compared to the cisplatin control, significant (p<0.01) increases in body weights were shown 13 and 14 days after the first drug administration, and significant increases in body weight gains during the total period of the experiment and the drug administration were also shown. Such results are considered as indirect evidence showing that the ondansetron and Pinelliae Rhizoma and Scutellariae Radix extract have an antioxidative effect at various degrees, and a protective effect at a certain degree on organ damage occurring all over the body caused by cisplatin, and then it was considered that the antioxidative and organ-protective effects on various organs had to be evaluated.

Example 3. Confirmation of Change in Charcoal Transit Ratio in Small Intestine (Gastrointestinal Motility)

In a digestive motility disorder, due to reduction in fecal excretion such as constipation and excessive water absorption caused by related fecal retention, it is known that water content in feces is considerably decreased, and fecal parameters such as a fecal pellet number and the water content in the feces have been used to evaluate effects of various drugs on the digestive motility disorder. Also, permeation of a substance through the digestive tract represents the motility in the entire gastrointestinal tract, measurement of a charcoal transit ratio in the small intestine is known to be very useful to diagnose whether or not there is a problem in digestive motility (Wintola et al., 2010), and a decrease in the charcoal transit ratio in the small intestine indicates a decrease in digestive motility such as the fecal retention, that is, constipation (Sagar et al., 2005; Meite et al., 2010).

Accordingly, in this example, changes in fecal parameters and the charcoal transit ratio in the small intestine caused by the ondansetron, and Pinelliae Rhizoma and Scutellariae Radix extract 200, 100 and 50 mg/kg administrations were examined.

A total length of a small intestine and a distance that a charcoal meal was transferred in the small intestine were measured, and the charcoal transit ratio was calculated, and then the results are shown in Table 4.

TABLE 4

Gastrointestinal motility (during 30 min)

| Groups | Total small intestine length (cm) | Distance charcoal meal transferred (cm) | GI charcoal transit ratio (%) |
|---|---|---|---|
| Controls | | | |
| Intact | 126.50 ± 5.78 | 95.88 ± 8.11 | 75.92 ± 7.06 |
| Cisplatin | 126.38 ± 6.48 | 45.00 ± 11.08$^a$ | 35.61 ± 8.66$^a$ |
| Reference | | | |
| Ondansetron | 128.63 ± 7.69 | 65.13 ± 10.68$^{ac}$ | 50.80 ± 8.85$^{ac}$ |
| PS orally administered | | | |
| 200 mg/kg | 124.88 ± 6.36 | 82.00 ± 11.25$^{bc}$ | 65.73 ± 8.58$^{bc}$ |
| 100 mg/kg | 126.63 ± 7.11 | 75.13 ± 14.8$^{ac}$ | 59.40 ± 11.61$^{ac}$ |
| 50 mg/kg | 126.88 ± 8.11 | 66.50 ± 11.20$^{ac}$ | 52.86 ± 10.89$^{ac}$ |

3.1. Change in Distance Charcoal Meal Transferred

Compared to the normal vehicle control, in the cisplatin control, a significant ($p<0.01$) decrease in the distance that the charcoal meal was transferred in the small intestine was shown, but in the ondansetron and three doses of Pinelliae Rhizoma and Scutellariae Radix extract administered groups, compared to the cisplatin control, a significant ($p<0.01$) increase in the distance that the charcoal meal was transferred in the small intestine was shown (Table 4).

In the cisplatin control, compared to the normal vehicle control, the distance that the charcoal meal was transferred in the small intestine changed by −53.06%, and in the ondansetron, and Pinelliae Rhizoma and Scutellariae Radix extract 200, 100 and 50 mg/kg-administered groups, compared to the cisplatin control, the distance that the charcoal meal was transferred in the small intestine changed by 44.72, 82.22, 66.94 and 47.78%, respectively.

3.2. Change in Charcoal Transit Ratio in Small Intestine

Compared to the normal vehicle control, in the cisplatin control, a significant ($p<0.01$) decrease in ratio of the distance that the charcoal meal was transferred to a total length of the small intestine, that is, a charcoal transit ratio in the small intestine—the digestive motility was shown, and in the ondansetron, Pinelliae Rhizoma and Scutellariae Radix extract 200, 100 and 50 mg/kg administered groups, compared to the cisplatin control, a significant ($p<0.01$) increase in the charcoal transit ratio in the small intestine was shown (Table 4).

In the cisplatin control, compared to the normal vehicle control, the charcoal transit ratio in the small intestine changed by −53.09%, and in the ondansetron, and Pinelliae Rhizoma and Scutellariae Radix extract 200, 100 and 50 mg/kg administered groups, compared to the cisplatin control, the charcoal transit ratio in the small intestine changed by 42.66, 84.56, 66.80 and 48.42%, respectively.

As seen from the result of Example 3, it was confirmed that 50 mg/kg of the Pinelliae Rhizoma and Scutellariae Radix extract shows fecal excretion and a hyperkinetic effect of the digestive tract at similar levels to those in the ondansetron 1 mg/kg subcutaneously administered group, and therefore the composition of the present invention can reduce a digestive motility disorder.

Example 4. Confirmation of Changes in Fecal Parameters

Fecal changes were observed, and fecal parameters are shown in Table 5.

TABLE 5

| | Fecal parameter | | | |
|---|---|---|---|---|
| Groups | Fecal pellet number | Wet-weight (g) | Dry-weight (g) | Water content (%) |
| Controls | | | | |
| Intact | 40.63 ± 10.70 | 20.33 ± 2.08 | 5.55 ± 1.27 | 72.17 ± 8.24 |
| Cisplatin | 15.75 ± 5.50$^a$ | 7.66 ± 2.14$^a$ | 5.14 ± 1.51 | 32.86 ± 6.45$^d$ |
| Reference | | | | |
| Ondansetron | 25.38 ± 6.95$^{ac}$ | 12.55 ± 3.71$^{ab}$ | 5.27 ± 1.10 | 55.32 ± 13.07$^{ef}$ |
| PS orally administered | | | | |
| 200 mg/kg | 36.63 ± 4.44$^b$ | 19.54 ± 1.52$^b$ | 5.66 ± 1.11 | 71.20 ± 3.67$^f$ |
| 100 mg/kg | 29.00 ± 8.85$^{ab}$ | 14.49 ± 5.07$^{ab}$ | 5.57 ± 1.60 | 60.41 ± 7.27$^{ef}$ |
| 50 mg/kg | 25.25 ± 6.09$^{ac}$ | 12.69 ± 3.14$^{ab}$ | 5.66 ± 1.13 | 54.30 ± 8.80$^{df}$ |

4.1. Confirmation of Change in Fecal Pellet Number

As a result of counting fecal pellet numbers excreted 33 to 34 days after the first cisplatin administration for 24 hours, compared to the normal vehicle control, in the cisplatin control, a significant ($p<0.01$) decrease in the fecal pellet number was shown, but in the ondansetron and all of the Pinelliae Rhizoma and Scutellariae Radix extract administered groups, compared to the cisplatin control, significant ($p<0.01$ or $p<0.05$) increases in the excreted fecal pellet number were shown (Table 5).

In the cisplatin control, compared to the normal vehicle control, a total number of fecal pellets excreted 33 to 34 days after the first cisplatin administration for 24 hours changed by −61.23%, and in the ondansetron, and Pinelliae Rhizoma and Scutellariae Radix extract 200, 100 and 50 mg/kg administered groups, compared to the cisplatin control, the total numbers of the fecal pellets changed by 61.11, 132.54, 84.13 and 60.32%, respectively.

4.2. Confirmation of Change in Wet Weight of Feces

Compared to the normal vehicle control, in the cisplatin control, a significant ($p<0.01$) decrease in the wet weight of feces was shown, and in the ondansetron, and Pinelliae Rhizoma and Scutellariae Radix extract 200, 100 and 50 mg/kg administered groups, compared to the cisplatin control, significant ($p<0.01$) increases in the wet weight of feces were shown (Table 5).

In the cisplatin control, compared to the normal vehicle control, an average wet weight of the feces excreted 33 to 34 days after the first cisplatin administration for 24 hours changed by −62.34%, and in the ondansetron, and Pinelliae Rhizoma and Scutellariae Radix extract 200, 100 and 50 mg/kg administered groups, compared to the cisplatin control, the average wet weights of the feces changed by 63.91, 155.19, 89.24 and 65.69%, respectively.

4.3. Confirmation of Changes in Dry Weights of Feces

As a result of the average dry weight of the feces excreted 33 to 34 days after the first cisplatin administration for 24 hours, compared to the normal vehicle control, no significant changes in the average dry weight of the feces were shown in all experimental groups in which a gastrointestinal motility disorder was caused by cisplatin, and in the ondansetron and Pinelliae Rhizoma and Scutellariae Radix extract administered groups, compared to the cisplatin control, no significant change in the dry weight of feces was shown (Table 5).

In the cisplatin control, compared to the normal vehicle control, an average dry weight of feces 33 to 34 days after the first cisplatin administration for 24 hours changed by −7.30%, and in the ondansetron, and Pinelliae Rhizoma and Scutellariae Radix extract 200, 100 and 50 mg/kg administered groups, compared to the cisplatin control, the average dry weight of the feces changed by 2.48, 10.48, 8.27 and 10.02%, respectively.

4.4. Confirmation of Change in Water Content in Feces

Compared to the normal vehicle control, in the cisplatin control, a significant (p<0.01) decrease in average water content in feces {[(the wet weight of feces−the dry weight of feces)/the wet weight of feces]×100} was shown, but in the ondansetron and all of three doses of the Pinelliae Rhizoma and Scutellariae Radix extract administered groups, compared to the cisplatin control, significant (p<0.01) increases in average water content in feces were shown (Table 5).

In the cisplatin control, compared to the normal vehicle control, the average water content in feces excreted 33 to 34 days after the first cisplatin administration for 24 hours changed by −54.47%, and in the ondansetron, and Pinelliae Rhizoma and Scutellariae Radix extract 200, 100 and 50 mg/kg administered groups, compared to the cisplatin control, the average water content in feces changed by 68.34, 116.68, 83.84 and 65.24%, respectively.

Example 5. Confirmation of Change in Antioxidative Defense System in Fundus

Changes in MDA content, GSH content, SOD activity, and CAT activity in the fundus in each group that were observed are shown in Table 6.

5.1. Confirmation of Change in Fundus MDA Content

Compared to the normal vehicle control, in the cisplatin control, a significant (p<0.01) increase in lipid peroxidation in fundus tissues, that is, the MDA content, was shown, and in the ondansetron, and Pinelliae Rhizoma and Scutellariae Radix extract 200, 100 and 50 mg/kg administered groups, compared to the cisplatin control, significant (p<0.01) decreases in MDA content in fundus tissues were shown (Table 6).

In the cisplatin control, compared to the normal vehicle control, the MDA content in fundus tissues at the final sacrifice changed by 327.30%, and in the ondansetron, and Pinelliae Rhizoma and Scutellariae Radix extract 200, 100 and 50 mg/kg administered groups, compared to the cisplatin control, the MDA content changed by −40.45, −59.42, −53.03 and −40.16%, respectively.

5.2. Confirmation of Change in Fundus GSH Content

Compared to the normal vehicle control, in the cisplatin control, a significant (p<0.01) decrease in content of an endogenous antioxidant, GSH, in fundus tissues was shown, and in the ondansetron and all of Pinelliae Rhizoma and Scutellariae Radix extract administered groups, compared to the cisplatin control, a significant (p<0.01) increase in GSH content in fundus tissues was shown (Table 6).

In the cisplatin control, compared to the normal vehicle control, the GSH content in the fundus tissue at the final sacrifice changed by −72.46%, and in the ondansetron, and Pinelliae Rhizoma and Scutellariae Radix extract 200, 100 and 50 mg/kg administered groups, compared to the cisplatin control, the GSH content changed by 48.11, 81.17, 60.90 and 46.06%, respectively.

5.3. Confirmation of Change in Fundus SOD Activity

Compared to the normal vehicle control, in the cisplatin control, a significant (p<0.01) decrease in activity of an endogenous antioxidant enzyme, SOD, in fundus tissues, was shown, but in the ondansetron and all of three doses of Pinelliae Rhizoma and Scutellariae Radix extract administered groups, compared to the cisplatin control, significant (p<0.01) increases in SOD activity in fundus tissues were shown (Table 6).

In the cisplatin control, compared to the normal vehicle control, the SOD activity in the fundus tissue at the final sacrifice changed by −56.87%, and in the ondansetron, and

TABLE 6

| | Fundus antioxidant defense system | | | |
|---|---|---|---|---|
| Groups | Malondialdehyde (nM/g tissue) | Glutathione (μM/mg tissue) | Catalase (nM/mim/mg tissue) | Superoxide dismutase (nM/mim/mg tissue) |
| Controls | | | | |
| Intact | 3.80 ± 1.73 | 4.43 ± 1.09 | 99.74 ± 13.66 | 166.83 ± 24.15 |
| Cisplatin | 16.24 ± 2.27$^a$ | 1.22 ± 0.40$^d$ | 44.06 ± 8.98$^a$ | 71.96 ± 15.54$^a$ |
| Reference | | | | |
| Ondansetron | 9.67 ± 1.93$^{ac}$ | 1.81 ± 0.17$^{de}$ | 63.48 ± 12.39$^{ac}$ | 103.00 ± 22.32$^{ac}$ |
| PS orally administered | | | | |
| 200 mg/kg | 6.59 ± 1.92$^{bc}$ | 2.21 ± 0.37$^{de}$ | 89.06 ± 14.94$^c$ | 130.94 ± 22.01$^{ac}$ |
| 100 mg/kg | 7.63 ± 2.50$^{ac}$ | 1.97 ± 0.20$^{de}$ | 73.77 ± 19.76$^{ac}$ | 116.89 ± 23.96$^{ac}$ |
| 50 mg/kg | 9.72 ± 1.94$^{ac}$ | 1.78 ± 0.31$^{de}$ | 63.38 ± 11.79$^{ac}$ | 102.77 ± 19.70$^{ac}$ |

Pinelliae Rhizoma and Scutellariae Radix extract 200, 100 and 50 mg/kg administered groups, compared to the cisplatin control, the SOD activities changed by 43.13, 81.96, 62.43 and 42.82%, respectively.

5.4. Confirmation of Change in Fundus CAT Activity

Compared to the normal vehicle control, in the cisplatin control, a significant ($p<0.01$) decrease in activity of an endogenous antioxidant enzyme, CAT, in fundus tissues was shown, but in the ondansetron, and Pinelliae Rhizoma and Scutellariae Radix extract 200, 100 and 50 mg/kg administered groups, compared to the cisplatin control, significant ($p<0.01$) increases in CAT activity in fundus tissues were shown (Table 6).

In the cisplatin control, compared to the normal vehicle control, the CAT activity in fundus tissues at the final sacrifice changed by −55.83%, and in the ondansetron, and Pinelliae Rhizoma and Scutellariae Radix extract 200, 100 and 50 mg/kg administered groups, compared to the cisplatin control, the CAT activities changed by 44.10, 95.34, 67.44 and 43.86%, respectively.

Figure 3:
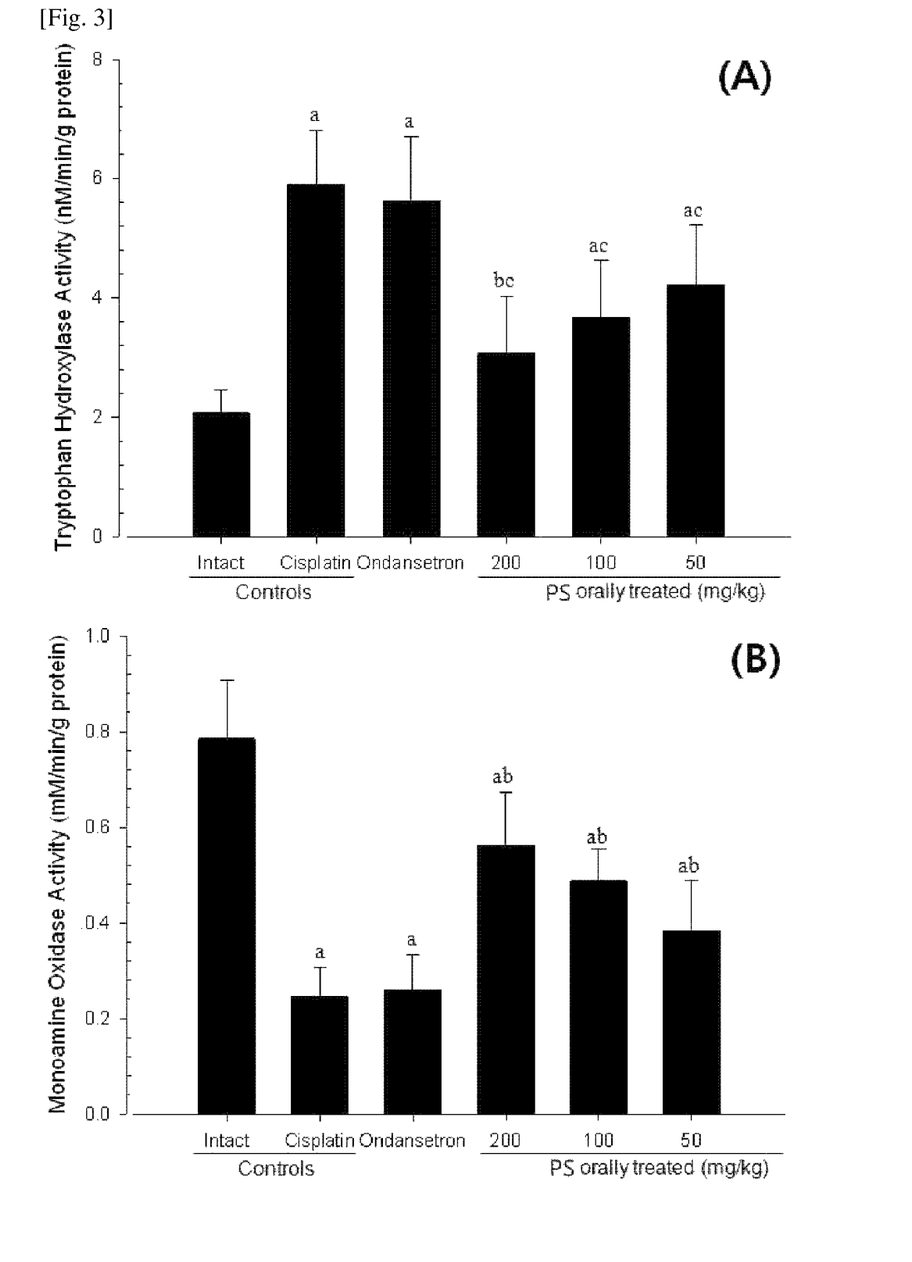
FIG. 3 shows the changes in tryptophan hydroxylase activity (A) and monoamine oxidase activity (B) in pyloric tissues of laboratory animals of each group.

Example 6. Confirmation of Change in Activities of Tryptophan Hydroxylase and Monoamine Oxidase 6.1. Confirmation of Change in Pylorus Tryptophan Hydroxylase Activity Compared to the normal vehicle control, in the cisplatin control, a significant ($p<0.01$) increase in activity of a serotonin synthase, tryptophan hydroxylase, in pyloric tissues was shown, but in all of the Pinelliae Rhizoma and Scutellariae Radix extract administered groups, compared to the cisplatin control, significant ($p<0.01$) decreases in tryptophan hydroxylase activity in pyloric tissues was dose-dependently shown. Meanwhile, in the ondansetron administered group, a change in tryptophan hydroxylase activity similar to that in the cisplatin control was shown (FIG. 3(A)).

In the cisplatin control, compared to the normal vehicle control, the tryptophan hydroxylase activity in pyloric tissues at the final sacrifice changed by 184.55%, and in the ondansetron, and Pinelliae Rhizoma and Scutellariae Radix extract 200, 100 and 50 mg/kg administered groups, compared to the cisplatin control, the tryptophan hydroxylase activity changed by −4.35, −48.02, −37.84 and −28.59%, respectively.

6.2. Confirmation of Change in Pylorus Monoamine Oxidase Activity

Compared to the normal vehicle control, in the cisplatin control, a significant ($p<0.01$) decrease in activity of a serotonin lyase, monoamine oxidase, in pyloric tissues was shown, but in the Pinelliae Rhizoma and Scutellariae Radix extract 200, 100 and 5 mg/kg administered groups, compared to the cisplatin control, significant ($p<0.01$) increases in monoamine oxidase activity in pyloric tissues were dose-dependently shown. Meanwhile, in the ondansetron administered group, a change in monoamine oxidase activity similar to that in the cisplatin control was shown (FIG. 3(B)).

In the cisplatin control, compared to the normal vehicle control, a monoamine oxidase activity in pyloric tissues at the final sacrifice changed by −68.47%, and in the ondansetron, Pinelliae Rhizoma and Scutellariae Radix extract 200, 100 and 50 mg/kg administered groups, compared to the cisplatin control, the monoamine oxidase activity changed by 5.05, 127.27, 96.97 and 55.05%, respectively.

Figure 4:
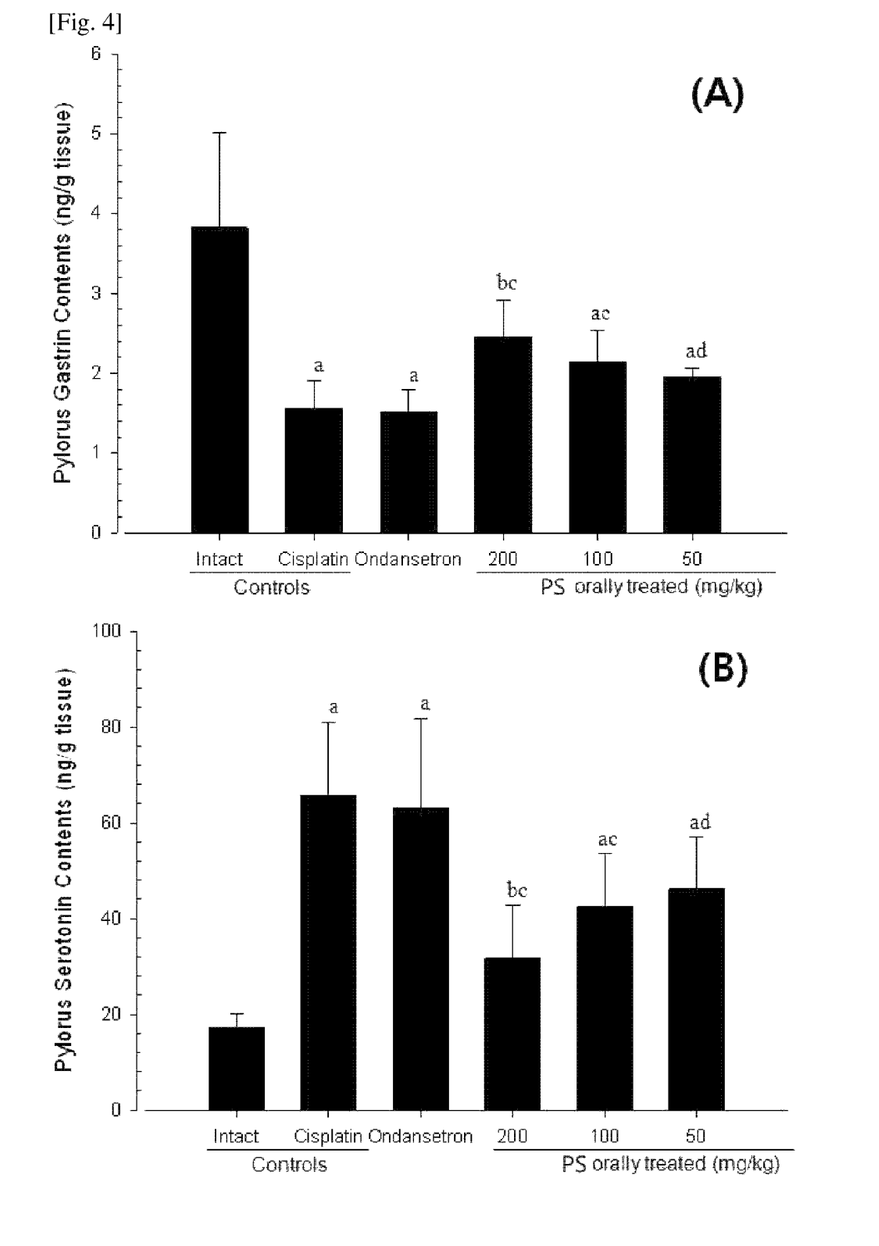
FIG. 4 shows the changes in gastrin contents (A) and serotonin contents (B) in pyloric tissues of laboratory animals of each group.

Example 7. Confirmation in Change of Gastrin and Serotonin Contents in Pyloric Tissues 7.1. Confirmation of Change in Pyloric Gastrin Content Compared to the normal vehicle control, in the cisplatin control, a significant ($p<0.01$) decrease in content of a digestive activity hormone, gastrin, in pyloric tissues was shown, but in all of three doses of the Pinelliae Rhizoma and Scutellariae Radix extract administered groups, compared to the cisplatin control, significant ($p<0.01$ or $p<0.05$) increases in gastrin content in pyloric tissues were dose-dependently shown. Meanwhile, in the ondansetron administered group, a change in pylorus gastrin content similar to that in the cisplatin control was shown (FIG. 4(A)).

In the cisplatin control, compared to the normal vehicle control, the gastrin content in pyloric tissues at the final sacrifice changed by −59.22%, and in the ondansetron, and Pinelliae Rhizoma and Scutellariae Radix extract 200, 100 and 50 mg/kg administered groups, compared to the cisplatin control, the gastrin content changed by −3.05, 57.82, 37.21 and 25.02%, respectively.

7.2. Confirmation of Change in Pylorus Serotonin Content

Compared to the normal vehicle control, in the cisplatin control, a significant ($p<0.01$) increase in serotonin content triggering inflammatory digestive mucosa damage in pyloric tissues was shown, but in the Pinelliae Rhizoma and Scutellariae Radix extract 200, 100 and 50 mg/kg administered groups, compared to the cisplatin control, significant ($p<0.01$ or $p<0.05$) decreases in serotonin content in pyloric tissues were dose-dependently shown. Meanwhile, in the ondansetron administered group, a change in pylorus serotonin content similar to that in the cisplatin control was shown (FIG. 4(B)).

In the cisplatin control, compared to the normal vehicle control, the change in serotonin content in pyloric tissues at the final sacrifice changed by 279.57%, and in the ondansetron, and Pinelliae Rhizoma and Scutellariae Radix extract 200, 100 and 50 mg/kg administered groups, compared to the cisplatin control, the serotonin contents changed by −4.04, −51.85, −35.29 and −29.90%, respectively.

Example 8. Confirmation of Histopathological Change

Fundus and pylorus thicknesses and thickness decreasing rates, measured by observing histopathological changes of the fundus, are shown in Table 7, and a colonic mucosa thickness, a mucous producing cell number, and a remaining fecal surface mucous thickness, measured by observing histopathological changes of the colon containing the fecal pellets, are shown in Table 8.

TABLE 7

| Groups | Fundus | | Pylorus | |
|---|---|---|---|---|
| | Total mucosa thickness (μm) | Degenerative mucosa percentage (%/mucosa) | Total mucosa thickness (μm) | Degenerative mucosa percentage (%/mucosa) |
| Controls | | | | |
| Intact | 830.95 ± 106.83 | 3.94 ± 2.31 | 381.72 ± 75.30 | 6.33 ± 3.57 |
| Cisplatin | 436.02 ± 87.18$^a$ | 54.89 ± 10.97$^d$ | 146.12 ± 26.03$^a$ | 68.26 ± 10.44$^a$ |
| Reference | | | | |
| Ondansetron | 592.37 ± 51.61$^{ac}$ | 35.42 ± 4.69$^{de}$ | 240.01 ± 36.08$^{ac}$ | 41.08 ± 10.77$^{ac}$ |
| PS orally administered | | | | |
| 200 mg/kg | 710.10 ± 104.82$^{bc}$ | 23.07 ± 3.11$^{de}$ | 315.61 ± 43.23$^{ac}$ | 20.10 ± 4.60$^{ac}$ |
| 100 mg/kg | 646.75 ± 105.29$^{ac}$ | 29.61 ± 2.52$^{de}$ | 279.07 ± 46.27$^{ac}$ | 33.55 ± 11.06$^{ac}$ |
| 50 mg/kg | 590.70 ± 76.22$^{ac}$ | 35.89 ± 9.00$^{de}$ | 237.86 ± 39.31$^{ac}$ | 42.30 ± 10.36$^{ac}$ |

TABLE 8

| Groups | Histomorphometry (at sacrifice) | | |
|---|---|---|---|
| | Fecal pellet surface mucous thickness (μm) | Mucous producing cell number (cells/mm$^2$) | Colonic mucosa thickness (μm) |
| Controls | | | |
| Intact | 54.88 ± 18.11 | 686.88 ± 135.16 | 280.15 ± 29.28 |
| Cisplatin | 8.24 ± 2.92$^d$ | 135.13 ± 53.54$^a$ | 111.63 ± 30.11$^a$ |
| Reference | | | |
| Ondansetron | 28.00 ± 6.98$^{df}$ | 306.63 ± 78.94$^{ac}$ | 192.08 ± 27.34$^{ac}$ |
| PS orally administered | | | |
| 200 mg/kg | 40.97 ± 10.06$^f$ | 533.38 ± 102.46$^{ac}$ | 239.74 ± 35.43$^{bc}$ |
| 100 mg/kg | 36.61 ± 8.82$^{ef}$ | 367.00 ± 100.38$^{ac}$ | 20.92 ± 33.48$^{ac}$ |
| 50 mg/kg | 27.98 ± 8.06$^{ef}$ | 303.50 ± 90.65$^{ac}$ | 189.01 ± 49.65$^{ac}$ |

8.1. Confirmation of Histopathological Change of Fundus

Figure 5:
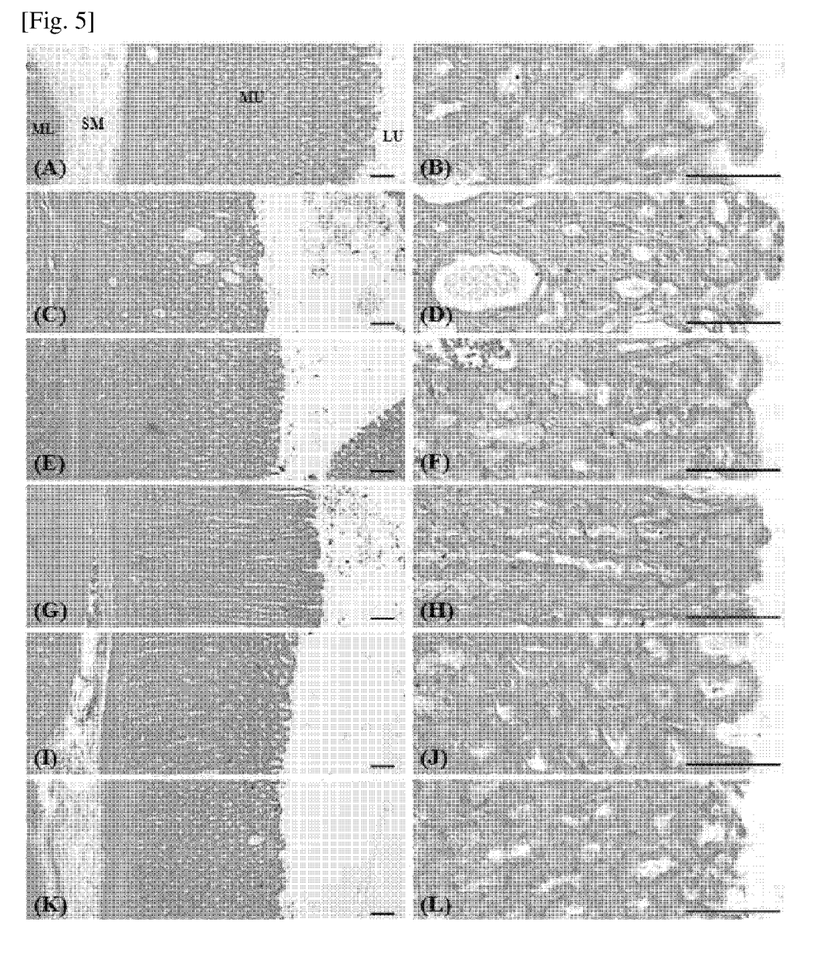
FIG. 5 is a schematic diagram showing the results of observing the fundus of laboratory animals of each group (A, B=Intact vehicle control, C, D=Cisplatin control, E, F=Ondansetron 1 mg/kg subcutaneously treated rat, G, H=Pinelliae Rhizoma and Scutellariae Radix extract 200 mg/kg orally treated rat, I, J=Pinelliae Rhizoma and Scutellariae Radix extract 100 mg/kg orally treated rat, K, L=Pinelliae Rhizoma and Scutellariae Radix extract 50 mg/kg orally treated rat; hereinafter, the same in FIGS. 6 and 7).

In the cisplatin control, focal erosive damage to a surface mucosa along with atrophy of the total fundic mucosa were caused, and thus, compared to the normal vehicle control, a significant (p<0.01) decrease in fundic mucosa thickness was shown, and a significant (p<0.01) increase in a degenerative fundic mucosa percentage [(Length of surface erosive pyloric mucosa/total surface pyloric mucosa length)× 100] was shown. Meanwhile, in the ondansetron, and Pinelliae Rhizoma and Scutellariae Radix extract 200, 100 and 50 mg/kg administered groups, cisplatin-induced fundic mucosa atrophy and focal erosion were considerably decreased, and compared to the cisplatin control, a significant (p<0.01) increase in fundic mucosa thickness and a decrease in the degenerative fundic mucosa percentage were shown (Table 7, and FIG. 5).

In the cisplatin control, compared to the normal vehicle control, a average fundic mucosa thickness changed by −47.53%, and in the ondansetron, and Pinelliae Rhizoma and Scutellariae Radix extract 200, 100 and 50 mg/kg administered groups, compared to the cisplatin control, the average fundic mucosa thickness changed by 35.86, 62.86, 48.33 and 35.48%, respectively.

In the cisplatin control, compared to the normal vehicle control, the degenerative fundic mucosa percentage changed by 1294.82%, and in the ondansetron, Pinelliae Rhizoma and Scutellariae Radix extract 200, 100 and 50 mg/kg administered groups, compared to the cisplatin control, the degenerative fundic mucosa percentage changed by −35.47, −57.98, −46.06 and −34.61%, respectively.

8.2. Confirmation of Fundus Histopathological Change

Figure 6:
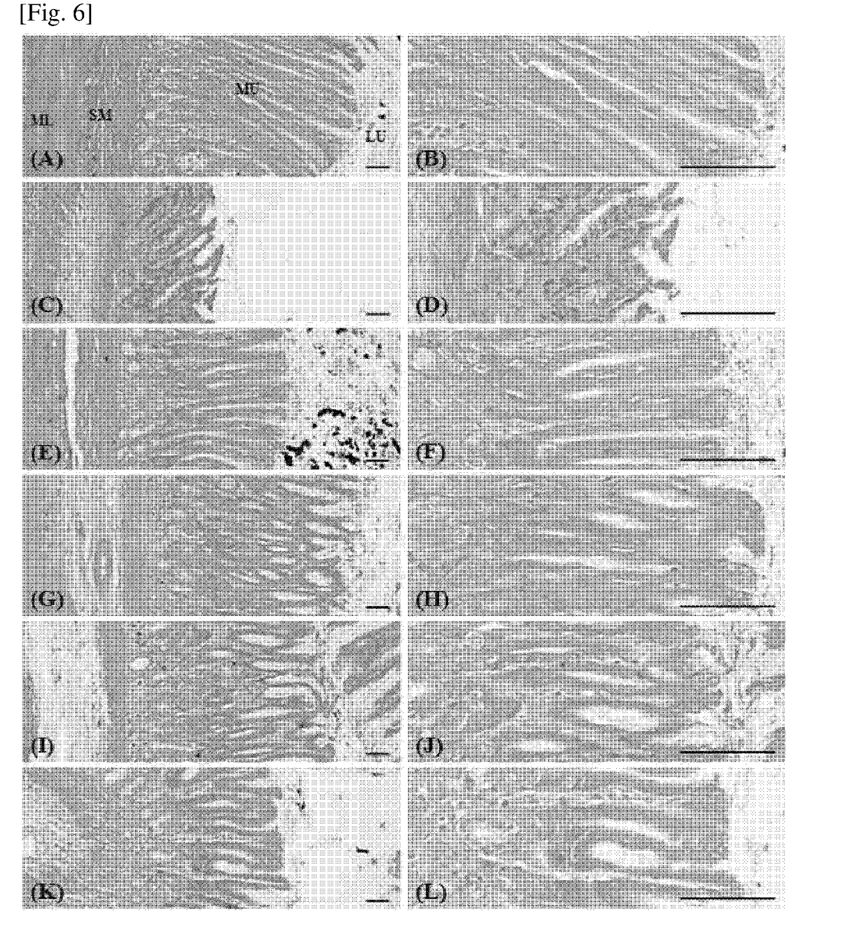
FIG. 6 shows the results of observing the pylorus of laboratory animals of each group.

In the cisplatin control, compared to the normal vehicle control, focal erosive damage to a surface mucosa along with atrophy of the total pyloric mucosa were caused, a significant (p<0.01) decrease in pyloric mucosa thickness was shown, and a significant (p<0.01) increase in a degenerative pyloric mucosa percentage was shown. Meanwhile, in the ondansetron and all of the Pinelliae Rhizoma and Scutellariae Radix extract administered groups, compared to the cisplatin control, cisplatin-induced atrophy of the pyloric mucosa and focal erosion were considerably decreased, and a significant (p<0.01) increase in pyloric mucosa thickness and a decrease in the degenerative pyloric mucosa percentage were shown (Table 7, and FIG. 6).

In the cisplatin control, compared to the normal vehicle control, the pylorus average mucosa thickness changed by −61.72%, and in the ondansetron, Pinelliae Rhizoma and Scutellariae Radix extract 200, 100 and 50 mg/kg administered groups, compared to the cisplatin control, the pylorus average mucosa thickness changed by 64.25, 115.99, 90.99 and 62.78%, respectively.

In the cisplatin control, compared to the normal vehicle control, the degenerative fundic mucosa percentage changed by 978.32%, and in the ondansetron, Pinelliae Rhizoma and Scutellariae Radix extract 200, 100 and 50 mg/kg administered groups, compared to the cisplatin control, the degenerative fundic mucosa percentage changed by −39.82, −70.56, −50.85 and −38.03%, respectively.

8.3. Confirmation of Histopathological Change in Colon Containing Fecal Pellets

Figure 7:
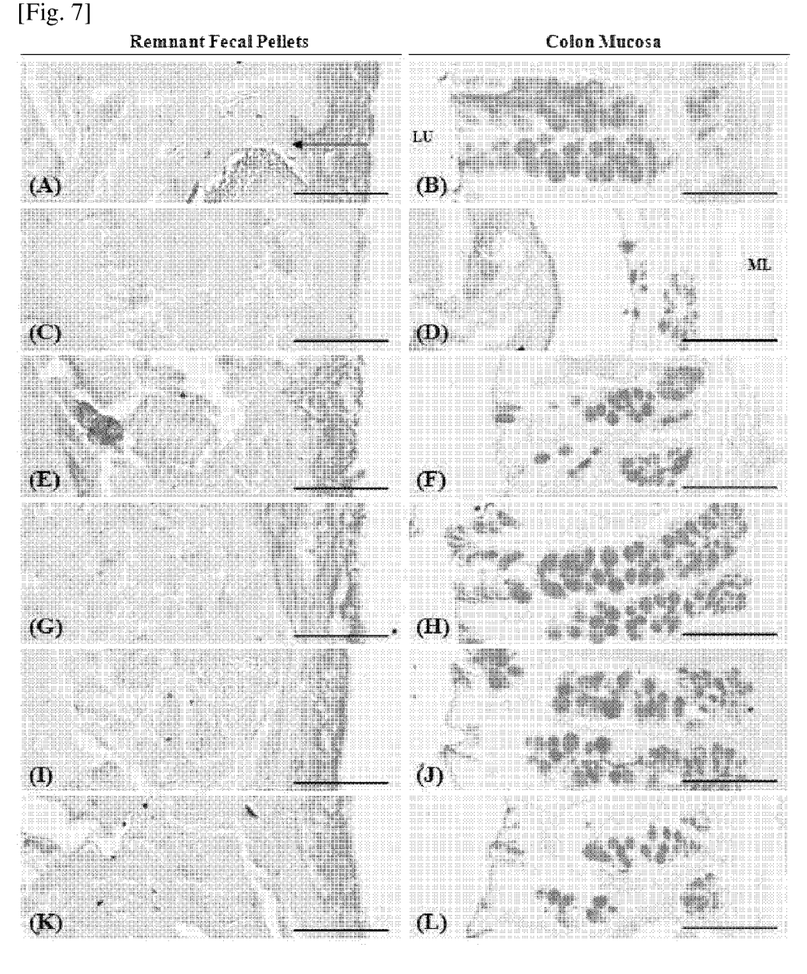
FIG. 7 shows the results of observing fecal pellet-containing colons of laboratory animals of each group.

In the cisplatin control, considerable decreases in the mucous producing cell number per unit area (mm$^2$) and fecal pellet surface mucous thickness were caused along with the atrophy of the total colonic mucosa containing fecal pellets, and thus, compared to the normal vehicle control, significant (p<0.01) decreases in fecal pellet-containing colonic mucosa thickness, the mucous producing cell number in the mucosa and fecal pellet surface mucous thickness were shown. Meanwhile, in the ondansetron and all of three doses of the Pinelliae Rhizoma and Scutellariae Radix extract administered groups, the decreases in atrophy of the cisplatin-induced colonic mucosa, the mucous producing cell number in the mucosa and the fecal pellet surface mucous thickness were considerably inhibited, and thus compared to the cisplatin control, significant (p<0.01) increases in colonic mucosa thickness, the mucous producing cell number and fecal pellet surface mucous thickness were shown (Table 8, and FIG. 7).

In the cisplatin control, compared to the normal vehicle control, the fecal pellet surface mucous thickness in the colon changed by −84.99%, and in the ondansetron, and Pinelliae Rhizoma and Scutellariae Radix extract 200, 100 and 50 mg/kg administered groups, compared to the cisplatin control, the fecal pellet surface mucous thickness changed by 239.94, 397.39, 344.39 and 239.61%, respectively.

In the cisplatin control, compared to the normal vehicle control, the mucous producing cell number in the colonic mucosa changed by −80.33%, and in the ondansetron, and Pinelliae Rhizoma and Scutellariae Radix extract 200, 100 and 50 mg/kg administered groups, compared to the cisplatin control, the mucous producing cell numbers changed by 126.92, 294.73, 171.60 and 124.61%, respectively.

In the cisplatin control, compared to the normal vehicle control, the fecal pellet-containing colon average mucosa thickness changed by −60.15%, and in the ondansetron, and Pinelliae Rhizoma and Scutellariae Radix extract 200, 100 and 50 mg/kg administered groups, compared to the cisplatin control, the fecal pellet-containing colon average mucosa thicknesses changed by 72.06, 114.75, 97.90 and 69.31%, respectively.

Example 9. Histopathological Change

As a result of observing histopathological changes, the numbers of gastrin and serotonin immunoreactive cells in the pyloric mucosa and the number of serotonin immunoreactive cells in the colonic mucosa that were detected are shown in Table 9.

TABLE 9

| Groups | Number of IR cells (cells/mm$^2$ of mucosa) | | |
| --- | --- | --- | --- |
| | Gastrin-IR cells in the pyloric mucosa | Serotonin-IR cells in the pyloric mucosa | Serotonin-IR cells in the colonic mucosa |
| Controls | | | |
| Intact | 86.50 ± 23.53 | 10.38 ± 2.33 | 12.00 ± 3.12 |
| Cisplatin | 11.75 ± 3.77$^d$ | 65.38 ± 11.02$^a$ | 73.75 ± 11.79$^a$ |
| Reference | | | |
| Ondansetron | 11.63 ± 3.70$^d$ | 64.00 ± 10.45$^a$ | 73.00 ± 17.65$^a$ |
| PS orally administered | | | |
| 200 mg/kg | 65.38 ± 14.16$^e$ | 19.88 ± 7.02$^c$ | 27.50 ± 11.22$^{bc}$ |
| 100 mg/kg | 54.50 ± 11.48$^{de}$ | 33.88 ± 13.87$^{ac}$ | 40.63 ± 16.88$^{ac}$ |
| 50 mg/kg | 21.75 ± 5.01$^{de}$ | 50.63 ± 10.97$^{ac}$ | 50.38 ± 16.79$^{ac}$ |

9.1. Confirmation of Change in Gastrin Immunoreactive Cells in Pyloric Mucosa

Figure 8:
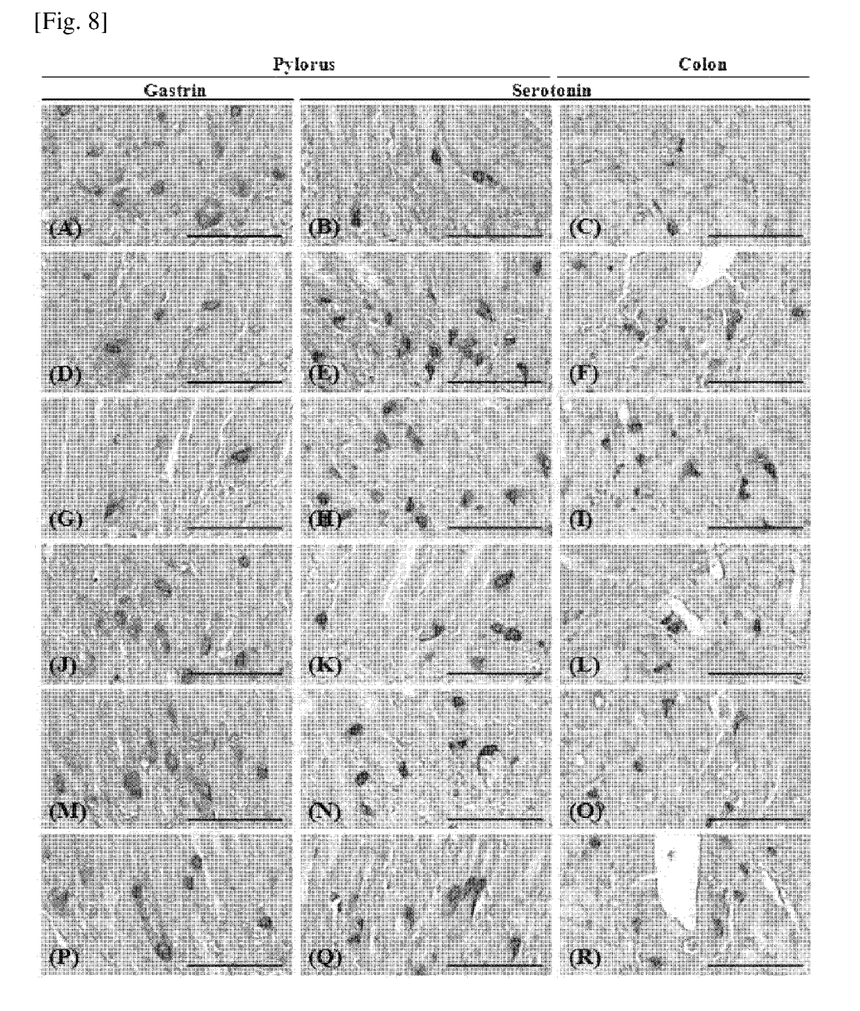
FIG. 8 shows the results of observing the pyloric mucosa of laboratory animals of each group (A~C=Intact vehicle control, D~F=Cisplatin control, G~I=Ondansetron 1 mg/kg subcutaneously treated rat, J~L=Pinelliae Rhizoma and Scutellariae Radix extract 200 mg/kg orally treated rat, M~O=Pinelliae Rhizoma and Scutellariae Radix extract 100 mg/kg orally treated rat, P~R=Pinelliae Rhizoma and Scutellariae Radix extract 50 mg/kg orally treated rat).

In the cisplatin control, compared to the normal vehicle control, a significant (p<0.01) decrease in the number of gastrin immunoreactive cells in the pyloric mucosa per unit area (mm$^2$) was shown, but in the Pinelliae Rhizoma and Scutellariae Radix extract 200, 100 and 50 mg/kg administered groups, compared to the cisplatin control, a significant (p<0.01) increase in the number of gastrin immunoreactive cells in the pyloric mucosa was dose-dependently shown. Meanwhile, in the ondansetron administered group, a change in the number of gastrin immunoreactive cells in the pyloric mucosa similar to that in the cisplatin control was shown (Table 9, and FIG. 8).

In the cisplatin control, compared to the normal vehicle control, the number of gastrin immunoreactive cells per unit area of the pyloric mucosa changed by −86.42%, and in the ondansetron, Pinelliae Rhizoma and Scutellariae Radix extract 200, 100 and 50 mg/kg administered groups, compared to the cisplatin control, the number of gastrin immunoreactive cells changed by −1.06, 456.38, 363.83 and 85.11%, respectively.

9.2. Confirmation of Change in Serotonin Immunoreactive Cells in Pyloric Mucosa

In the cisplatin control, compared to the normal vehicle control, a significant (p<0.01) increase in the number of serotonin immunoreactive cells per unit area of the pyloric mucosa (mm$^2$) was shown, but in all of three doses of the Pinelliae Rhizoma and Scutellariae Radix extract administered groups, compared to the cisplatin control, significant (p<0.01) decreases in the number of serotonin immunoreactive cells in the pyloric mucosa were dose-dependently shown. Meanwhile, in the ondansetron administered group, a numerical change in serotonin immunoreactive cells in the pyloric mucosa similar to that in the cisplatin control was shown (Table 9, and FIG. 8).

In the cisplatin control, compared to the normal vehicle control, the number of serotonin immunoreactive cells per unit area of the pyloric mucosa changed by 530.12%, and in the ondansetron, and Pinelliae Rhizoma and Scutellariae Radix extract 200, 100 and 50 mg/kg administered groups, compared to the cisplatin control, the number of serotonin immunoreactive cells changed by −2.10, −69.60, −48.18 and −22.56%, respectively.

9.3. Confirmation of Change in Serotonin Immunoreactive Cells in Colonic Mucosa

In the cisplatin control, compared to the normal vehicle control, a significant (p<0.01) increase in the number of serotonin immunoreactive cells per unit area of the colonic mucosa (mm$^2$) was shown, but in all of the Pinelliae Rhizoma and Scutellariae Radix extract administered groups, compared to the cisplatin control, significant (p<0.01) numerical decreases in serotonin immunoreactive cells in the colonic mucosa were dose-dependently shown. Meanwhile, in the ondansetron administered group, the numerical change in serotonin immunoreactive cells in the colonic mucosa similar to that in the cisplatin control was shown (Table 9, and FIG. 8).

In the cisplatin control, compared to the normal vehicle control, the number of serotonin immunoreactive cells per unit area of the colonic mucosa changed by 514.58%, and in the ondansetron, and Pinelliae Rhizoma and Scutellariae Radix extract 200, 100 and 50 mg/kg administered groups, compared to the cisplatin control, the number of serotonin immunoreactive cells changed by −1.02, −62.71, −44.92 and −31.69%, respectively.

As seen from the result of Example 9, it was seen that the 200, 100 and 50 mg/kg of Pinelliae Rhizoma and Scutellariae Radix extracts normalize the cisplatin-induced increase in activity of tryptophan hydroxylase and the inhibition of monoamine oxidase activity, but the ondansetron known as a typical 5-HT$_3$ receptor blocking agent did not significantly influence the activities of tryptophan hydroxylase and monoamine oxidase involved in the synthesis and degradation of serotonin in tissues.

As seen from the result of the example, it was seen that the administration of 50, 100 or 200 mg/kg of the Pinelliae Rhizoma and Scutellariae Radix extract after the cisplatin administration as described above has a useful effect on gastrointestinal tract damage caused by cisplatin and a motility disorder through antioxidation and synthesis and secretion or control of functions of gastrin and serotonin producing gastrointestinal tract endocrine cells, and oral administration of 50 mg/kg of the Pinelliae Rhizoma and Scutellariae Radix extract had an effect of reducing a cisplatin-induced digestive disorder at a similar degree to subcutaneous administration of 1 mg/kg of ondansetron.

Therefore, it was confirmed that 50 mg/kg or more of the Pinelliae Rhizoma and Scutellariae Radix extract can very effectively control the digestive disorder caused when various chemotherapeutic agents including cisplatin are administered to a patient with a neoplastic disease, and have an excellent effect of reducing a side effect of a chemotherapeutic agent for a patient with a neoplastic disease.

It would be understood by those of ordinary skill in the art that the above descriptions of the present invention are exemplary, and the example embodiments disclosed herein can be easily modified into other specific forms without changing the technical spirit or essential features of the present invention. Therefore, it should be interpreted that the example embodiments described above are exemplary in all aspects, and are not limitative.

The invention claimed is:

1. A method for reducing a cisplatin-induced digestive disorder comprising:
    administering an effective amount of a pharmaceutical composition consisting essentially of
        Pinelliae Rhizoma and Scutellariae Radix extract as active ingredients, and
        a pharmaceutically acceptable carrier selected from the group consisting of distilled water, a saline solution, polyethyleneglycol, ethanol, a vegetable oil, or isopropylmyristate.

2. The method of claim 1, wherein a mixed weight ratio (w/w) of the Pinelliae Rhizoma and Scutellariae Radix extract is 0.1 to 5: 0.5 to 6.

3. The method of claim 1, wherein a mixed weight ratio (w/w) of the Pinelliae Rhizoma and Scutellariae Radix extract is 1 to 3: 2 to 4.

* * * * *